United States Patent
Courtis et al.

(10) Patent No.: US 11,051,829 B2
(45) Date of Patent: Jul. 6, 2021

(54) CUSTOMIZED PATIENT-SPECIFIC ORTHOPAEDIC SURGICAL INSTRUMENT

(71) Applicant: DePuy Synthes Products, Inc., Raynham, MA (US)

(72) Inventors: R. Patrick Courtis, Boston, MA (US); Francis Metelues, Warsaw, IN (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 141 days.

(21) Appl. No.: 16/018,137

(22) Filed: Jun. 26, 2018

(65) Prior Publication Data
US 2019/0388240 A1    Dec. 26, 2019

(51) Int. Cl.
| | |
|---|---|
| *A61B 17/15* | (2006.01) |
| *A61B 17/17* | (2006.01) |
| *A61B 17/56* | (2006.01) |
| *A61F 2/46* | (2006.01) |
| *A61B 34/10* | (2016.01) |

(52) U.S. Cl.
CPC .......... *A61B 17/155* (2013.01); *A61B 17/154* (2013.01); *A61B 17/1764* (2013.01); *A61B 17/56* (2013.01); *A61F 2/461* (2013.01); *A61F 2/4607* (2013.01); *A61B 17/1746* (2013.01); *A61B 2017/568* (2013.01); *A61B 2034/102* (2016.02); *A61B 2034/108* (2016.02); *A61F 2/4609* (2013.01)

(58) Field of Classification Search
CPC .................................................. A61B 17/155
See application file for complete search history.

(56) References Cited

U.S. PATENT DOCUMENTS

| | | |
|---|---|---|
| 2,702,550 A | 2/1955 | Rowe |
| 3,229,372 A | 1/1966 | Quashnock et al. |
| 3,298,410 A | 1/1967 | Morifuji |
| 3,624,747 A | 11/1971 | Gilbert et al. |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

Accuracy of CT-Based Patient Specific Total Knee Arthroplasty Instruments; AAHKS 20th Annual Meeting, Submission Record, Submission ID # 4177, Apr. 14, 2010.

(Continued)

*Primary Examiner* — Nicholas W Woodall
(74) *Attorney, Agent, or Firm* — Barnes & Thornburg LLP

(57) ABSTRACT

An orthopaedic surgical instrument includes a customized patient-specific surgical instrument having a body. A cutting guide slot extends through the body. A pair of first arms extends posteriorly from the body. Each arm includes a first customized patient-specific negative contour configured to receive a portion of a first corresponding positive contour of one of a patient's femoral condyles. A second arm extends proximally from the body. The second arm has a second customized patient-specific negative contour configured to receive a portion of a second corresponding positive contour of an anterior surface of the patient's femur. A method of performing a surgical procedure is also disclosed.

6 Claims, 7 Drawing Sheets

(56) References Cited

U.S. PATENT DOCUMENTS

| | | |
|---|---|---|
| 3,685,720 A | 8/1972 | Brady |
| 3,698,017 A | 10/1972 | Scales et al. |
| 3,774,244 A | 11/1973 | Walker |
| 3,816,855 A | 6/1974 | Saleh |
| 3,840,904 A | 10/1974 | Tronzo |
| 3,869,731 A | 3/1975 | Waugh et al. |
| 3,901,298 A | 8/1975 | Eby |
| 3,903,549 A | 9/1975 | Deyerle |
| 3,920,022 A | 11/1975 | Pastor |
| 3,941,127 A | 3/1976 | Froning |
| 3,965,950 A | 6/1976 | MacDonald |
| 3,994,287 A | 11/1976 | Turp et al. |
| 4,055,862 A | 11/1977 | Farling |
| 4,081,866 A | 4/1978 | Upshaw et al. |
| 4,085,466 A | 4/1978 | Goodfellow et al. |
| 4,140,161 A | 2/1979 | Russo et al. |
| 4,197,886 A | 4/1980 | MacDonald |
| 4,311,145 A | 1/1982 | Esty et al. |
| 4,349,018 A | 9/1982 | Chambers |
| 4,373,709 A | 2/1983 | Whitt |
| 4,386,609 A | 6/1983 | Mongeon |
| 4,400,833 A | 8/1983 | Kurland |
| 4,436,684 A | 3/1984 | White |
| D273,895 S | 5/1984 | Kenna |
| D274,091 S | 5/1984 | Kenna |
| 4,475,549 A | 10/1984 | Oh |
| 4,501,269 A | 2/1985 | Bagby |
| 4,506,393 A | 3/1985 | Murphy |
| 4,509,518 A | 4/1985 | McGarry et al. |
| 4,524,766 A | 6/1985 | Petersen |
| 4,534,365 A | 8/1985 | Bonetta et al. |
| 4,545,375 A | 10/1985 | Cline |
| 4,549,555 A | 10/1985 | Fraser et al. |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,583,554 A | 4/1986 | Mittelman et al. |
| 4,583,555 A | 4/1986 | Malcom et al. |
| 4,621,630 A | 11/1986 | Kenna |
| 4,632,111 A | 12/1986 | Roche |
| 4,641,648 A | 2/1987 | Shapiro |
| 4,646,729 A | 3/1987 | Kenna et al. |
| 4,653,488 A | 3/1987 | Kenna et al. |
| 4,662,372 A | 5/1987 | Sharkany et al. |
| 4,663,720 A | 5/1987 | Duret et al. |
| 4,695,283 A | 9/1987 | Aldinger |
| 4,703,751 A | 11/1987 | Pohl |
| 4,704,686 A | 11/1987 | Aldinger |
| 4,711,233 A | 12/1987 | Brown |
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,739,751 A | 4/1988 | Sapega et al. |
| 4,759,350 A | 7/1988 | Dunn et al. |
| 4,787,383 A | 11/1988 | Kenna |
| 4,791,934 A | 12/1988 | Brunnett |
| 4,800,874 A | 1/1989 | David et al. |
| 4,822,365 A | 4/1989 | Walker et al. |
| 4,834,080 A | 5/1989 | Brown |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,860,735 A | 8/1989 | Davey et al. |
| 4,888,022 A | 12/1989 | Huebsch |
| 4,893,619 A | 1/1990 | Dale et al. |
| 4,896,663 A | 1/1990 | Vandewalls |
| 4,911,721 A | 3/1990 | Aendergaten et al. |
| 4,913,163 A | 4/1990 | Roger et al. |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker |
| 4,938,762 A | 7/1990 | Wehrli |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 5,002,579 A | 3/1991 | Copf et al. |
| 5,007,912 A | 4/1991 | Albrektsson et al. |
| 5,007,936 A | 4/1991 | Woolson |
| 5,015,247 A | 5/1991 | Michelson |
| 5,030,221 A | 7/1991 | Buechel et al. |
| 5,032,132 A | 7/1991 | Matsen et al. |
| 5,035,700 A | 7/1991 | Kenna |
| 5,041,117 A | 8/1991 | Engelhardt |
| 5,053,037 A | 10/1991 | Lackey |
| 5,053,039 A | 10/1991 | Hofmann et al. |
| 5,060,678 A | 10/1991 | Bauman et al. |
| 5,061,286 A | 10/1991 | Lyle |
| 5,062,843 A | 11/1991 | Mahony, III |
| 5,067,964 A | 11/1991 | Richmond et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,100,689 A | 3/1992 | Goldberg et al. |
| 5,108,401 A | 4/1992 | Insall et al. |
| 5,111,987 A | 5/1992 | Moeinzadeh et al. |
| 5,122,144 A | 6/1992 | Bert et al. |
| 5,123,906 A | 6/1992 | Kelman |
| 5,129,908 A | 7/1992 | Petersen |
| 5,129,909 A | 7/1992 | Sutherland |
| 5,133,660 A | 7/1992 | Fenick |
| 5,133,760 A | 7/1992 | Petersen et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,186,174 A | 2/1993 | Schlondorff et al. |
| 5,192,327 A | 3/1993 | Brantigan |
| 5,197,488 A | 3/1993 | Kovacevic |
| 5,197,971 A | 3/1993 | Bonutti |
| 5,197,987 A | 3/1993 | Koch et al. |
| 5,207,680 A | 5/1993 | Dietz et al. |
| 5,207,692 A | 5/1993 | Kraus et al. |
| 5,211,165 A | 5/1993 | Dumoulin et al. |
| 5,217,463 A | 6/1993 | Michael |
| 5,228,459 A | 7/1993 | Caspari et al. |
| 5,234,433 A | 8/1993 | Bert et al. |
| 5,242,448 A | 9/1993 | Pettine et al. |
| 5,251,635 A | 10/1993 | Dumoulin et al. |
| 5,255,680 A | 10/1993 | Darrow et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,265,610 A | 11/1993 | Darrow et al. |
| 5,269,785 A | 12/1993 | Bonutti |
| 5,273,524 A | 12/1993 | Fox et al. |
| 5,274,565 A | 12/1993 | Reuben |
| 5,275,603 A | 1/1994 | Ferrante et al. |
| 5,282,803 A | 2/1994 | Lackey |
| 5,285,773 A | 2/1994 | Bonutti et al. |
| 5,299,288 A | 3/1994 | Glassman et al. |
| 5,300,077 A | 4/1994 | Howell |
| 5,304,181 A | 4/1994 | Caspari et al. |

(56) References Cited

U.S. PATENT DOCUMENTS

| | | |
|---|---|---|
| 5,305,244 A | 4/1994 | Newman et al. |
| 5,308,349 A | 5/1994 | Mikhail |
| 5,314,478 A | 5/1994 | Oka et al. |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,360,016 A | 11/1994 | Kovacevic |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,382,249 A | 1/1995 | Fletcher |
| 5,383,454 A | 1/1995 | Bucholz |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |
| D358,647 S | 5/1995 | Cohen et al. |
| 5,415,662 A | 5/1995 | Ferrante et al. |
| 5,417,694 A | 5/1995 | Marik et al. |
| 5,423,827 A | 6/1995 | Mumme et al. |
| 5,423,828 A | 6/1995 | Benson |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,452,407 A | 9/1995 | Crook |
| 5,454,816 A | 10/1995 | Ashby |
| 5,456,268 A | 10/1995 | Bonutti |
| 5,458,645 A | 10/1995 | Bertin |
| 5,462,549 A | 10/1995 | Glock |
| 5,470,354 A | 11/1995 | Hershberger et al. |
| 5,472,415 A | 12/1995 | King et al. |
| 5,474,559 A | 12/1995 | Bertin et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | Defonzo et al. |
| 5,507,833 A | 4/1996 | Bohn |
| 5,510,066 A | 4/1996 | Fink et al. |
| 5,513,972 A | 5/1996 | Schroeder et al. |
| 5,514,139 A | 5/1996 | Goldstein et al. |
| 5,514,143 A | 5/1996 | Bonutti et al. |
| 5,514,519 A | 5/1996 | Neckers |
| 5,518,680 A | 5/1996 | Cima et al. |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,542,947 A | 8/1996 | Treacy |
| 5,549,683 A | 8/1996 | Bonutti |
| 5,554,190 A | 9/1996 | Draenert |
| 5,560,096 A | 10/1996 | Stephens |
| 5,562,674 A | 10/1996 | Stalcup et al. |
| 5,562,675 A | 10/1996 | McNulty et al. |
| 5,569,163 A | 10/1996 | Francis et al. |
| 5,569,261 A | 10/1996 | Marik et al. |
| 5,571,110 A | 11/1996 | Matsen, III et al. |
| 5,578,037 A | 11/1996 | Sanders et al. |
| 5,578,039 A | 11/1996 | Vendrely et al. |
| 5,586,558 A | 12/1996 | Riley et al. |
| 5,593,448 A | 1/1997 | Dong |
| 5,595,703 A | 1/1997 | Swaelens et al. |
| 5,597,379 A | 1/1997 | Haines et al. |
| 5,601,563 A | 2/1997 | Burke et al. |
| 5,601,566 A | 2/1997 | Dance et al. |
| 5,607,431 A | 3/1997 | Dudasik et al. |
| 5,609,603 A | 3/1997 | Linden |
| 5,620,448 A | 4/1997 | Puddu |
| 5,624,444 A | 4/1997 | Wixon et al. |
| 5,632,745 A | 5/1997 | Schwartz |
| 5,634,927 A | 6/1997 | Houston et al. |
| 5,643,272 A | 7/1997 | Haines et al. |
| 5,649,947 A | 7/1997 | Auerbach et al. |
| 5,653,714 A | 8/1997 | Dietz et al. |
| 5,658,294 A | 8/1997 | Sederholm |
| 5,662,656 A | 9/1997 | White |
| 5,667,511 A | 9/1997 | Vendrely et al. |
| 5,667,512 A | 9/1997 | Johnson |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,397 A | 11/1997 | Vendrely et al. |
| 5,683,398 A | 11/1997 | Carls et al. |
| 5,683,466 A | 11/1997 | Vitale |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,690,638 A | 11/1997 | Dance et al. |
| 5,701,370 A | 12/1997 | Muhs et al. |
| 5,702,447 A | 12/1997 | Walch et al. |
| 5,702,460 A | 12/1997 | Carls et al. |
| 5,702,475 A | 12/1997 | Zahedi |
| 5,704,941 A | 1/1998 | Jacober et al. |
| 5,707,350 A | 1/1998 | Krause et al. |
| 5,711,299 A | 1/1998 | Manwaring et al. |
| 5,716,360 A | 2/1998 | Baldwin et al. |
| 5,719,743 A | 2/1998 | Jenkins et al. |
| 5,719,744 A | 2/1998 | Jenkins et al. |
| 5,720,752 A | 2/1998 | Elliott et al. |
| 5,722,978 A | 3/1998 | Jenkins |
| 5,725,376 A | 3/1998 | Poirier |
| 5,725,593 A | 3/1998 | Caracciolo |
| 5,733,292 A | 3/1998 | Gustilo et al. |
| 5,735,277 A | 4/1998 | Schuster |
| 5,738,345 A | 4/1998 | Schroeder et al. |
| 5,748,767 A | 5/1998 | Raab |
| 5,749,875 A | 5/1998 | Puddu |
| 5,749,876 A | 5/1998 | Duvillier et al. |
| 5,755,803 A | 5/1998 | Haines et al. |
| 5,757,339 A | 5/1998 | Williams et al. |
| 5,762,125 A | 6/1998 | Mastrorio |
| 5,768,134 A | 6/1998 | Swaelens et al. |
| 5,769,855 A | 6/1998 | Bertin et al. |
| 5,776,201 A | 7/1998 | Colleran et al. |
| 5,788,700 A | 8/1998 | Morawa et al. |
| 5,791,212 A | 8/1998 | Han |
| 5,792,143 A | 8/1998 | Samuelson et al. |
| 5,798,924 A | 8/1998 | Eufinger et al. |
| 5,799,055 A | 8/1998 | Peshkin et al. |
| 5,799,099 A | 8/1998 | Wang et al. |
| 5,810,827 A | 9/1998 | Haines et al. |
| 5,810,829 A | 9/1998 | Elliott et al. |
| 5,810,831 A | 9/1998 | D'Antonio |
| 5,817,097 A | 10/1998 | Howard et al. |
| 5,824,085 A | 10/1998 | Sahay et al. |
| 5,844,656 A | 12/1998 | Ronzani et al. |
| 5,844,824 A | 12/1998 | Newman et al. |
| 5,860,980 A | 1/1999 | Axelson, Jr. et al. |
| 5,860,981 A | 1/1999 | Bertin et al. |
| 5,869,170 A | 2/1999 | Cima et al. |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,393 A | 3/1999 | Whiteside et al. |
| 5,879,402 A | 3/1999 | Lawes et al. |
| 5,885,296 A | 3/1999 | Masini |
| 5,885,297 A | 3/1999 | Matsen, III |
| 5,885,298 A | 3/1999 | Herrington et al. |
| 5,895,389 A | 4/1999 | Schenk et al. |

(56) References Cited

U.S. PATENT DOCUMENTS

| | | |
|---|---|---|
| 5,897,559 A | 4/1999 | Masini |
| 5,899,907 A | 5/1999 | Johnson |
| 5,899,914 A | 5/1999 | Zirps et al. |
| 5,901,060 A | 5/1999 | Schall et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,925,049 A | 7/1999 | Gustilo et al. |
| 5,942,370 A | 8/1999 | Neckers |
| 5,967,777 A | 10/1999 | Klein et al. |
| 5,967,980 A | 10/1999 | Ferre et al. |
| 5,976,149 A | 11/1999 | Masini |
| 5,980,526 A | 11/1999 | Johnson et al. |
| 5,989,261 A | 11/1999 | Walker et al. |
| 6,007,537 A | 12/1999 | Burkinshaw et al. |
| 6,012,456 A | 1/2000 | Schuerch |
| 6,019,767 A | 2/2000 | Howell |
| 6,022,350 A | 2/2000 | Ganem |
| 6,024,746 A | 2/2000 | Katz |
| 6,033,415 A | 3/2000 | Mittelstadt et al. |
| 6,034,296 A | 3/2000 | Elvin et al. |
| 6,056,754 A | 5/2000 | Haines et al. |
| 6,056,756 A | 5/2000 | Eng et al. |
| 6,059,831 A | 5/2000 | Braslow et al. |
| 6,063,095 A | 5/2000 | Wang et al. |
| 6,066,075 A | 5/2000 | Poulton |
| 6,077,270 A | 6/2000 | Katz |
| 6,077,287 A | 6/2000 | Taylor et al. |
| 6,080,196 A | 6/2000 | Bertin |
| 6,081,577 A | 6/2000 | Webber |
| 6,086,593 A | 7/2000 | Bonutti |
| 6,090,122 A | 7/2000 | Sjostrom et al. |
| 6,096,043 A | 8/2000 | Techiera et al. |
| 6,099,313 A | 8/2000 | Doerken et al. |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,139,574 A | 10/2000 | Vacanti et al. |
| 6,146,390 A | 11/2000 | Heilbrun et al. |
| 6,156,069 A | 12/2000 | Amstutz |
| 6,156,070 A | 12/2000 | Incavo et al. |
| 6,159,246 A | 12/2000 | Mendes et al. |
| 6,161,080 A | 12/2000 | Aouni-Ateshian et al. |
| 6,165,181 A | 12/2000 | Heilbrun et al. |
| 6,167,145 A | 12/2000 | Foley et al. |
| 6,176,874 B1 | 1/2001 | Vacanti et al. |
| 6,177,034 B1 | 1/2001 | Ferrone |
| 6,185,315 B1 | 2/2001 | Schmucker et al. |
| 6,187,010 B1 | 2/2001 | Masini |
| 6,195,615 B1 | 2/2001 | Lysen |
| 6,197,064 B1 | 3/2001 | Haines et al. |
| 6,198,794 B1 | 3/2001 | Peshkin et al. |
| 6,205,411 B1 | 3/2001 | DiGioia et al. |
| 6,206,927 B1 | 3/2001 | Fell et al. |
| 6,214,051 B1 | 4/2001 | Badorf et al. |
| 6,220,122 B1 | 4/2001 | Forsell et al. |
| 6,228,121 B1 | 5/2001 | Khalili |
| 6,241,671 B1 | 6/2001 | Ritter et al. |
| 6,241,735 B1 | 6/2001 | Marmulla |
| 6,244,141 B1 | 6/2001 | Han |
| 6,246,900 B1 | 6/2001 | Cosman et al. |
| 6,251,143 B1 | 6/2001 | Schwartz et al. |
| 6,254,604 B1 | 7/2001 | Howell |
| 6,258,127 B1 | 7/2001 | Schmotzer |
| 6,264,698 B1 | 7/2001 | Lawes et al. |
| 6,273,891 B1 | 8/2001 | Masini |
| 6,277,136 B1 | 8/2001 | Bonutti |
| 6,285,902 B1 | 9/2001 | Kienzle, III et al. |
| 6,290,703 B1 | 9/2001 | Ganem |
| 6,290,704 B1 | 9/2001 | Burkinshaw et al. |
| 6,301,593 B1 | 10/2001 | Toyosato |
| 6,314,310 B1 | 11/2001 | Ben-Haim et al. |
| 6,319,006 B1 | 11/2001 | Scherer et al. |
| 6,322,728 B1 | 11/2001 | Brodkin et al. |
| 6,325,806 B1 | 12/2001 | Fox |
| 6,327,491 B1 | 12/2001 | Franklin et al. |
| 6,341,231 B1 | 1/2002 | Ferre et al. |
| 6,343,987 B2 | 2/2002 | Hayama et al. |
| 6,351,659 B1 | 2/2002 | Vilsmeier |
| 6,354,011 B1 | 3/2002 | Albrecht |
| 6,361,506 B1 | 3/2002 | Saenger et al. |
| 6,370,224 B1 | 4/2002 | Simon et al. |
| 6,382,975 B1 | 5/2002 | Poirier |
| 6,383,221 B1 | 5/2002 | Scarborough et al. |
| 6,383,228 B1 | 5/2002 | Schmotzer |
| 6,391,251 B1 | 5/2002 | Keicher et al. |
| 6,395,005 B1 | 5/2002 | Lovell |
| 6,405,072 B1 | 6/2002 | Cosman |
| 6,406,495 B1 | 6/2002 | Schoch |
| 6,409,722 B1 | 6/2002 | Hoey et al. |
| 6,421,232 B2 | 7/2002 | Sallam |
| 6,424,856 B1 | 7/2002 | Vilsmeier et al. |
| 6,427,698 B1 | 8/2002 | Yoon |
| 6,430,434 B1 | 8/2002 | Mittelstadt |
| 6,434,415 B1 | 8/2002 | Foley et al. |
| 6,442,416 B1 | 8/2002 | Schultz |
| D462,767 S | 9/2002 | Meyer et al. |
| 6,445,943 B1 | 9/2002 | Ferre et al. |
| 6,454,811 B1 | 9/2002 | Sherwood et al. |
| 6,458,135 B1 | 10/2002 | Harwin et al. |
| 6,459,948 B1 | 10/2002 | Ateshian et al. |
| 6,461,359 B1 | 10/2002 | Tribus et al. |
| 6,463,351 B1 | 10/2002 | Clynch |
| 6,463,361 B1 | 10/2002 | Wang et al. |
| 6,468,280 B1 | 10/2002 | Saenger et al. |
| 6,468,289 B1 | 10/2002 | Bonutti |
| 6,474,341 B1 | 11/2002 | Hunter et al. |
| 6,478,799 B1 | 11/2002 | Williamson |
| 6,482,209 B1 | 11/2002 | Engh et al. |
| 6,490,467 B1 | 12/2002 | Bucholz et al. |
| 6,491,702 B2 | 12/2002 | Heilbrun et al. |
| 6,493,573 B1 | 12/2002 | Martinelli et al. |
| 6,496,099 B2 | 12/2002 | Wang et al. |
| 6,499,488 B1 | 12/2002 | Hunter et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,516,212 B1 | 2/2003 | Bladen et al. |
| 6,520,964 B2 | 2/2003 | Tallarida et al. |
| 6,530,958 B1 | 3/2003 | Cima et al. |
| 6,532,482 B1 | 3/2003 | Toyosato |
| 6,533,737 B1 | 3/2003 | Brosseau et al. |
| 6,535,756 B1 | 3/2003 | Simon et al. |
| 6,545,279 B1 | 4/2003 | Yoshida et al. |
| 6,552,899 B2 | 4/2003 | Ronzani et al. |
| 6,554,837 B1 | 4/2003 | Hauri et al. |
| 6,554,838 B2 | 4/2003 | McGovern et al. |
| 6,556,008 B2 | 4/2003 | Thesen |
| 6,558,391 B2 | 5/2003 | Axelson et al. |
| 6,567,681 B1 | 5/2003 | Lindequist |
| 6,575,980 B1 | 6/2003 | Robie et al. |
| 6,575,982 B1 | 6/2003 | Bonutti |
| 6,584,174 B2 | 6/2003 | Schubert et al. |
| 6,591,581 B2 | 7/2003 | Schmieding |
| 6,602,259 B1 | 8/2003 | Masini |
| 6,625,563 B2 | 9/2003 | Kirsch et al. |
| 6,626,945 B2 | 9/2003 | Simon et al. |
| 6,629,999 B1 | 10/2003 | Serafin |
| 6,632,225 B2 | 10/2003 | Sanford et al. |
| 6,633,773 B1 | 10/2003 | Reisfeld |
| 6,635,073 B2 | 10/2003 | Bonutti |
| 6,640,127 B1 | 10/2003 | Kosaka et al. |
| 6,642,836 B1 | 11/2003 | Wang et al. |
| 6,646,541 B1 | 11/2003 | Wang et al. |
| 6,662,036 B2 | 12/2003 | Cosman |
| 6,668,941 B2 | 12/2003 | Phillips et al. |
| 6,673,077 B1 | 1/2004 | Katz |
| 6,676,662 B1 | 1/2004 | Bagga et al. |

(56) References Cited

U.S. PATENT DOCUMENTS

| | | |
|---|---|---|
| 6,679,917 B2 | 1/2004 | Ek |
| 6,687,531 B1 | 2/2004 | Ferre et al. |
| 6,695,848 B2 | 2/2004 | Haines |
| 6,697,664 B2 | 2/2004 | Kienzle, III et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,824 B2 | 3/2004 | Millard et al. |
| 6,712,856 B1 | 3/2004 | Carignan et al. |
| 6,716,249 B2 | 4/2004 | Hyde |
| 6,724,922 B1 | 4/2004 | Vilsmeier |
| 6,725,077 B1 | 4/2004 | Balloni et al. |
| 6,725,080 B2 | 4/2004 | Melkent et al. |
| 6,738,656 B1 | 5/2004 | Ferre et al. |
| 6,738,657 B1 | 5/2004 | Franklin et al. |
| 6,740,092 B2 | 5/2004 | Lombardo et al. |
| 6,743,258 B1 | 6/2004 | Keller |
| 6,749,638 B1 | 6/2004 | Saladino |
| 6,750,653 B1 | 6/2004 | Zou et al. |
| 6,766,878 B2 | 7/2004 | Widmer et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,798,391 B2 | 9/2004 | Peterson |
| 6,799,066 B2 | 9/2004 | Steines et al. |
| 6,814,735 B1 | 11/2004 | Zirngibl et al. |
| 6,827,723 B2 | 12/2004 | Carson |
| 6,847,336 B1 | 1/2005 | Lemelson et al. |
| 6,859,660 B2 | 2/2005 | Vilsmeier |
| 6,873,867 B2 | 3/2005 | Vilsmeier |
| 6,892,090 B2 | 5/2005 | Verard et al. |
| 6,905,514 B2 | 6/2005 | Carignan et al. |
| 6,916,324 B2 | 7/2005 | Sanford et al. |
| 6,918,907 B2 | 7/2005 | Kelly et al. |
| 6,920,347 B2 | 7/2005 | Simon et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,934,575 B2 | 8/2005 | Ferre et al. |
| 6,942,475 B2 | 9/2005 | Ensign et al. |
| 6,944,518 B2 | 9/2005 | Roose |
| 6,945,976 B2 | 9/2005 | Ball et al. |
| 6,947,786 B2 | 9/2005 | Simon et al. |
| 6,953,480 B2 | 10/2005 | Mears et al. |
| 6,968,846 B2 | 11/2005 | Viswanathan |
| 6,978,166 B2 | 12/2005 | Foley et al. |
| 6,979,299 B2 | 12/2005 | Peabody et al. |
| 6,990,220 B2 | 1/2006 | Ellis et al. |
| 6,994,549 B2 | 2/2006 | Brodkin et al. |
| 7,029,477 B2 | 4/2006 | Grimm |
| 7,029,479 B2 | 4/2006 | Tallarida et al. |
| 7,033,361 B2 | 4/2006 | Collazo |
| 7,048,741 B2 | 5/2006 | Swanson |
| 7,050,877 B2 | 5/2006 | Iseki et al. |
| 7,060,074 B2 | 6/2006 | Rosa et al. |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,172,597 B2 | 2/2007 | Sanford |
| 7,172,599 B2 | 2/2007 | Steffensmeier et al. |
| 7,175,435 B2 | 2/2007 | Andersson et al. |
| 7,176,466 B2 | 2/2007 | Rousso et al. |
| 7,184,814 B2 | 2/2007 | Lang et al. |
| 7,194,295 B2 | 3/2007 | Vilsmeier |
| 7,198,628 B2 | 4/2007 | Ondrla et al. |
| 7,235,080 B2 | 6/2007 | Hodorek |
| 7,239,908 B1 | 7/2007 | Alexander et al. |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,371,260 B2 | 5/2008 | Malinin |
| 7,383,164 B2 | 6/2008 | Aram et al. |
| 7,388,972 B2 | 6/2008 | Kitson |
| 7,392,076 B2 | 6/2008 | Moctezuma de La Barrera |
| 7,427,272 B2 | 9/2008 | Richard et al. |
| 7,474,223 B2 | 1/2009 | Nycz et al. |
| 7,481,780 B2 | 1/2009 | De Guise et al. |
| 7,488,324 B1 | 2/2009 | Metzger et al. |
| 7,527,631 B2 | 5/2009 | Maroney et al. |
| 7,534,263 B2 | 5/2009 | Burdulis, Jr. et al. |
| 7,539,243 B1 | 5/2009 | Toifl et al. |
| 7,542,791 B2 | 6/2009 | Mire et al. |
| 7,543,239 B2 | 6/2009 | Viswanathan et al. |
| 7,575,602 B2 | 8/2009 | Amirouche et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,632,279 B2 | 12/2009 | Bastian |
| 7,634,119 B2 | 12/2009 | Tsougarakis et al. |
| 7,641,663 B2 | 1/2010 | Hodorek |
| 7,651,501 B2 | 1/2010 | Penenberg et al. |
| 7,661,170 B2 | 2/2010 | Goode et al. |
| 7,695,477 B2 | 4/2010 | Creger et al. |
| 7,704,253 B2 | 4/2010 | Bastian et al. |
| 7,717,956 B2 | 5/2010 | Lang |
| 7,780,672 B2 | 8/2010 | Metzger et al. |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,824,181 B2 | 11/2010 | Sers |
| 7,881,768 B2 | 2/2011 | Lang et al. |
| 7,887,595 B1 | 2/2011 | Pimenta |
| 7,935,119 B2 | 5/2011 | Ammann et al. |
| 7,963,968 B2 | 6/2011 | Dees, Jr. |
| 7,967,868 B2 | 6/2011 | White et al. |
| 7,981,158 B2 | 7/2011 | Fitz et al. |
| 7,985,225 B2 | 7/2011 | Johnson et al. |
| 7,988,691 B2 | 8/2011 | Schulze et al. |
| 8,077,950 B2 | 12/2011 | Tsougarakis et al. |
| 8,092,465 B2 | 1/2012 | Metzger et al. |
| 8,122,582 B2 | 2/2012 | Burdulis, Jr. et al. |
| 8,162,949 B2 | 4/2012 | Duggineni et al. |
| 8,265,949 B2 | 9/2012 | Haddad |
| 8,311,306 B2 | 11/2012 | Pavlovskaia et al. |
| 8,323,288 B2 | 12/2012 | Zajac |
| 8,343,159 B2 | 1/2013 | Bennett |
| 8,357,166 B2 | 1/2013 | Aram et al. |
| 8,361,076 B2 | 1/2013 | Roose et al. |
| 8,366,771 B2 | 2/2013 | Burdulis, Jr. et al. |
| 8,369,926 B2 | 2/2013 | Lang et al. |
| 8,377,068 B2 | 2/2013 | Aker et al. |
| 8,377,141 B2 | 2/2013 | McMinn |
| 8,398,645 B2 | 3/2013 | Aker et al. |
| 8,398,646 B2 | 3/2013 | Metzger et al. |
| 8,419,740 B2 | 4/2013 | Aram et al. |
| 8,425,523 B2 | 4/2013 | Aram et al. |
| 8,425,524 B2 | 4/2013 | Aker et al. |
| 8,444,651 B2 | 5/2013 | Kunz et al. |
| 8,457,930 B2 | 6/2013 | Schroeder |
| 8,460,303 B2 | 6/2013 | Park |
| 8,480,679 B2 | 7/2013 | Park et al. |
| 8,480,754 B2 | 7/2013 | Bojarski et al. |
| 8,483,469 B2 | 7/2013 | Pavlovskaia et al. |
| 8,532,361 B2 | 9/2013 | Pavlovskaia et al. |
| 8,532,806 B1 | 9/2013 | Masson |
| D691,719 S | 10/2013 | Park |
| 8,560,047 B2 | 10/2013 | Haider et al. |
| 8,591,516 B2 | 11/2013 | Metzger et al. |
| 8,594,395 B2 | 11/2013 | Roose et al. |

(56) References Cited

U.S. PATENT DOCUMENTS

| | | |
|---|---|---|
| 8,617,171 B2 | 12/2013 | Park et al. |
| 8,617,175 B2 | 12/2013 | Park et al. |
| 8,634,617 B2 | 1/2014 | Tsougarakis et al. |
| 8,702,712 B2 | 4/2014 | Jordan et al. |
| 8,715,291 B2 | 5/2014 | Park et al. |
| 8,734,455 B2 | 5/2014 | Park et al. |
| 8,737,700 B2 | 5/2014 | Park et al. |
| 8,764,759 B2 | 7/2014 | Dees, Jr. |
| 8,777,875 B2 | 7/2014 | Park |
| 8,784,495 B2 | 7/2014 | Bonutti |
| 8,794,977 B2 | 8/2014 | McGuan et al. |
| 8,834,473 B2 | 9/2014 | Dees, Jr. et al. |
| 8,834,490 B2 | 9/2014 | Bonutti |
| 8,932,363 B2 | 1/2015 | Tsougarakis et al. |
| 8,965,088 B2 | 2/2015 | Tsougarakis et al. |
| 8,968,321 B2 | 3/2015 | Wright et al. |
| 8,974,459 B1 | 3/2015 | Keelson, Jr. et al. |
| 8,979,855 B2 | 3/2015 | Aram et al. |
| 9,017,336 B2 | 4/2015 | Park et al. |
| 9,044,249 B2 | 6/2015 | Dees, Jr. |
| 9,066,728 B2 | 6/2015 | Burdulis, Jr. et al. |
| 9,095,353 B2 | 8/2015 | Burdulis, Jr. et al. |
| 9,101,393 B2 | 8/2015 | Jordan et al. |
| 9,173,662 B2 | 11/2015 | Aram et al. |
| 9,314,251 B2 | 4/2016 | Aram et al. |
| 9,408,619 B2 | 8/2016 | Salehi et al. |
| 9,498,199 B2 | 11/2016 | Colquhoun et al. |
| 9,532,788 B2 | 1/2017 | Jordan et al. |
| 9,649,205 B2 | 5/2017 | Dees, Jr. |
| 9,786,022 B2 | 10/2017 | Aram et al. |
| 9,861,387 B2 | 1/2018 | Metzger et al. |
| 10,028,750 B2 | 7/2018 | Rose |
| 10,149,722 B2 | 12/2018 | Aram et al. |
| 10,631,878 B2 * | 4/2020 | Fritzinger ............ A61B 17/155 |
| 2001/0005797 A1 | 6/2001 | Barlow et al. |
| 2001/0016775 A1 | 8/2001 | Scarborough et al. |
| 2001/0018589 A1 | 8/2001 | Muller |
| 2001/0020143 A1 | 9/2001 | Stark et al. |
| 2001/0034554 A1 | 10/2001 | Pappas |
| 2001/0037155 A1 | 11/2001 | Merchant |
| 2001/0039421 A1 | 11/2001 | Heilbrun et al. |
| 2002/0007294 A1 | 1/2002 | Bradbury et al. |
| 2002/0024450 A1 | 2/2002 | Townsend et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087062 A1 | 7/2002 | Schmidt et al. |
| 2002/0087274 A1 | 7/2002 | Alexander et al. |
| 2002/0143279 A1 | 10/2002 | Porier et al. |
| 2002/0147415 A1 | 10/2002 | Martelli |
| 2002/0173797 A1 | 11/2002 | Van Zile et al. |
| 2002/0183610 A1 | 12/2002 | Foley et al. |
| 2002/0183760 A1 | 12/2002 | McGovern et al. |
| 2002/0188194 A1 | 12/2002 | Cosman |
| 2002/0198529 A1 | 12/2002 | Masini |
| 2002/0198531 A1 | 12/2002 | Millard et al. |
| 2003/0009234 A1 | 1/2003 | Treacy et al. |
| 2003/0009354 A1 | 1/2003 | Arbogast et al. |
| 2003/0011624 A1 | 1/2003 | Ellis |
| 2003/0018338 A1 | 1/2003 | Axelson, Jr. et al. |
| 2003/0028196 A1 | 2/2003 | Bonutti |
| 2003/0055501 A1 | 3/2003 | Fell et al. |
| 2003/0055502 A1 | 3/2003 | Lang et al. |
| 2003/0069897 A1 | 4/2003 | Roy et al. |
| 2003/0074248 A1 | 4/2003 | Braud et al. |
| 2003/0088179 A1 | 5/2003 | Seeley et al. |
| 2003/0100906 A1 | 5/2003 | Rosa et al. |
| 2003/0100907 A1 | 5/2003 | Rosa et al. |
| 2003/0109784 A1 | 6/2003 | Loh et al. |
| 2003/0120183 A1 | 6/2003 | Simmons |
| 2003/0130665 A1 | 7/2003 | Pinczewski et al. |
| 2003/0158606 A1 | 8/2003 | Coon et al. |
| 2003/0171757 A1 | 9/2003 | Coon et al. |
| 2003/0181935 A1 | 9/2003 | Gardeski et al. |
| 2003/0212403 A1 | 11/2003 | Swanson |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0039259 A1 | 2/2004 | Krause et al. |
| 2004/0039394 A1 | 2/2004 | Conti et al. |
| 2004/0039395 A1 | 2/2004 | Coon et al. |
| 2004/0068187 A1 | 4/2004 | Krause et al. |
| 2004/0073279 A1 | 4/2004 | Malackowski et al. |
| 2004/0092932 A1 | 5/2004 | Aubin et al. |
| 2004/0098133 A1 | 5/2004 | Carignan et al. |
| 2004/0102785 A1 | 5/2004 | Hodorek et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0117015 A1 | 6/2004 | Biscup |
| 2004/0122439 A1 | 6/2004 | Dwyer et al. |
| 2004/0122787 A1 | 6/2004 | Avinash et al. |
| 2004/0122790 A1 | 6/2004 | Walker et al. |
| 2004/0124964 A1 | 7/2004 | Wang et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0167531 A1 | 8/2004 | Hodorek |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0185422 A1 | 9/2004 | Orth et al. |
| 2004/0204760 A1 | 10/2004 | Fitz et al. |
| 2004/0220583 A1 | 11/2004 | Pieczynski, II et al. |
| 2004/0236424 A1 | 11/2004 | Berez et al. |
| 2004/0243481 A1 | 12/2004 | Bradbury et al. |
| 2004/0249385 A1 | 12/2004 | Faoro |
| 2004/0249675 A1 | 12/2004 | Stark et al. |
| 2004/0254584 A1 | 12/2004 | Sarin et al. |
| 2004/0260301 A1 | 12/2004 | Lionberger et al. |
| 2005/0015003 A1 | 1/2005 | Lachner et al. |
| 2005/0015022 A1 | 1/2005 | Richard et al. |
| 2005/0027303 A1 | 2/2005 | Lionberger et al. |
| 2005/0027361 A1 | 2/2005 | Reiley |
| 2005/0037320 A1 | 2/2005 | Poirier |
| 2005/0043835 A1 | 2/2005 | Christensen |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0065628 A1 | 3/2005 | Roose |
| 2005/0070897 A1 | 3/2005 | Petersen |
| 2005/0075641 A1 | 4/2005 | Singhatat et al. |
| 2005/0096535 A1 | 5/2005 | de la Barrera |
| 2005/0113840 A1 | 5/2005 | Metzger et al. |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0133955 A1 | 6/2005 | Christensen |
| 2005/0137708 A1 | 6/2005 | Clark |
| 2005/0148843 A1 | 7/2005 | Roose |
| 2005/0149042 A1 | 7/2005 | Metzger |
| 2005/0170311 A1 | 8/2005 | Tardieu et al. |
| 2005/0171545 A1 | 8/2005 | Walsh et al. |
| 2005/0177170 A1 | 8/2005 | Fisher et al. |
| 2005/0182315 A1 | 8/2005 | Ritter et al. |
| 2005/0192588 A1 | 9/2005 | Garcia |
| 2005/0203536 A1 | 9/2005 | Laffargue et al. |
| 2005/0203540 A1 | 9/2005 | Broyles |
| 2005/0222573 A1 | 10/2005 | Branch et al. |
| 2005/0234461 A1 | 10/2005 | Burdulis et al. |

(56) References Cited

U.S. PATENT DOCUMENTS

| | | |
|---|---|---|
| 2005/0234465 A1 | 10/2005 | McCombs et al. |
| 2005/0234468 A1 | 10/2005 | Carson |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0261697 A1 | 11/2005 | Canonaco et al. |
| 2005/0267485 A1 | 12/2005 | Cordes et al. |
| 2005/0267584 A1 | 12/2005 | Burdulis et al. |
| 2005/0273113 A1 | 12/2005 | Kuczynski |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095049 A1 | 5/2006 | Zannis et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0142671 A1 | 6/2006 | Solak |
| 2006/0142774 A1 | 6/2006 | Metzger |
| 2006/0142778 A1 | 6/2006 | Dees |
| 2006/0155380 A1 | 7/2006 | Clemow et al. |
| 2006/0161167 A1 | 7/2006 | Myers et al. |
| 2006/0172261 A1 | 8/2006 | Garry |
| 2006/0173463 A1 | 8/2006 | Dees |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0229723 A1 | 10/2006 | Van Hoeck |
| 2006/0235421 A1 | 10/2006 | Rosa et al. |
| 2006/0245627 A1 | 11/2006 | Nagamune |
| 2006/0265078 A1 | 11/2006 | McMinn |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2007/0006887 A1 | 1/2007 | Frank |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0059665 A1 | 3/2007 | Orentlicher et al. |
| 2007/0066917 A1 | 3/2007 | Hodorek et al. |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0156066 A1 | 7/2007 | McGinley et al. |
| 2007/0162039 A1 | 7/2007 | Wozencroft |
| 2007/0167741 A1 | 7/2007 | Sherman et al. |
| 2007/0173946 A1 | 7/2007 | Bonutti |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0213738 A1 | 9/2007 | Martin et al. |
| 2007/0219560 A1 | 9/2007 | Hodorek |
| 2007/0219639 A1 | 9/2007 | Otto et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288030 A1 | 12/2007 | Metzger et al. |
| 2008/0009952 A1 | 1/2008 | Hodge |
| 2008/0015602 A1 | 1/2008 | Axelson |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021567 A1 | 1/2008 | Meulink et al. |
| 2008/0027563 A1 | 1/2008 | Johnson et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0114370 A1 | 5/2008 | Schoenefeld |
| 2008/0140081 A1 | 6/2008 | Heavener et al. |
| 2008/0140209 A1 | 6/2008 | Iannotti et al. |
| 2008/0146969 A1 | 6/2008 | Kurtz |
| 2008/0147072 A1 | 6/2008 | Park et al. |
| 2008/0161815 A1 | 7/2008 | Schoenefeld et al. |
| 2008/0172125 A1 | 7/2008 | Ek |
| 2008/0183177 A1 | 7/2008 | Fox et al. |
| 2008/0195099 A1 | 8/2008 | Minas |
| 2008/0195107 A1 | 8/2008 | Cuckler et al. |
| 2008/0195216 A1 | 8/2008 | Philipp |
| 2008/0208200 A1 | 8/2008 | Crofford |
| 2008/0215059 A1 | 9/2008 | Carignan et al. |
| 2008/0228189 A1 | 9/2008 | Fox et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294266 A1 | 11/2008 | Steinberg |
| 2008/0300600 A1 | 12/2008 | Guelat et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0082770 A1 | 3/2009 | Worner et al. |
| 2009/0087276 A1 | 4/2009 | Rose |
| 2009/0088674 A1 | 4/2009 | Caillouette et al. |
| 2009/0088753 A1* | 4/2009 | Aram .................. A61B 17/157 606/79 |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0089081 A1 | 4/2009 | Haddad |
| 2009/0093816 A1 | 4/2009 | Roose et al. |

(56) References Cited

U.S. PATENT DOCUMENTS

| | | |
|---|---|---|
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0220610 A1 | 9/2009 | Schmidt et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0264890 A1 | 10/2009 | Duggineni et al. |
| 2009/0270868 A1 | 10/2009 | Park et al. |
| 2009/0270869 A1 | 10/2009 | Colquhoun et al. |
| 2009/0274350 A1 | 11/2009 | Pavlovskaia et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2010/0016947 A1 | 1/2010 | Dobak, III |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0168857 A1 | 7/2010 | Hatch |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0324692 A1 | 12/2010 | Uthgenannt et al. |
| 2011/0004317 A1 | 1/2011 | Hacking et al. |
| 2011/0015636 A1 | 1/2011 | Katrana et al. |
| 2011/0015639 A1 | 1/2011 | Metzger et al. |
| 2011/0029091 A1 | 2/2011 | Bojarski et al. |
| 2011/0029093 A1* | 2/2011 | Bojarski ............... A61F 2/3859 623/20.35 |
| 2011/0029116 A1 | 2/2011 | Jordan et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0125009 A1 | 5/2011 | Lang et al. |
| 2011/0213378 A1 | 9/2011 | Dees, Jr. |
| 2011/0293581 A1 | 12/2011 | Lee et al. |
| 2012/0029520 A1 | 2/2012 | Lang et al. |
| 2012/0065640 A1 | 3/2012 | Metzger et al. |
| 2012/0093377 A1 | 4/2012 | Tsougarakis et al. |
| 2012/0158001 A1 | 6/2012 | Burdulis, Jr. et al. |
| 2013/0006661 A1 | 1/2013 | Haddad |
| 2013/0197527 A1 | 8/2013 | Nadzadi et al. |
| 2013/0197529 A1 | 8/2013 | Metzger et al. |
| 2013/0211409 A1 | 8/2013 | Burdulis, Jr. et al. |
| 2014/0018813 A1 | 1/2014 | McKinnon et al. |
| 2014/0153798 A1 | 6/2014 | Tsougarakis et al. |
| 2014/0163568 A1 | 6/2014 | Wong et al. |
| 2014/0200902 A1* | 7/2014 | Aram ..................... G06Q 50/22 705/2 |
| 2014/0222407 A1 | 8/2014 | Jordan et al. |
| 2014/0309645 A1 | 10/2014 | Dees, Jr. |
| 2015/0190145 A1 | 7/2015 | Aram et al. |
| 2015/0216615 A1 | 8/2015 | Tsougarakis et al. |
| 2015/0238273 A1 | 8/2015 | Jordan et al. |
| 2015/0257900 A1 | 9/2015 | Dees, Jr. |
| 2016/0174994 A1 | 6/2016 | Hafez |
| 2018/0325526 A1 | 11/2018 | Haddad |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CH | 117960 A | 5/1927 |
| CN | 1175893 A | 3/1998 |
| CN | 1181696 A | 5/1998 |
| CN | 1184409 A | 6/1998 |
| CN | 1342060 A | 3/2002 |
| CN | 1630495 A | 6/2005 |
| CN | 1728976 A | 2/2006 |
| CN | 1729483 A | 2/2006 |
| CN | 1729484 A | 2/2006 |
| CN | 1780594 A | 5/2006 |
| CN | 1913844 A | 2/2007 |
| CN | 101111197 A | 1/2008 |
| CN | 101466317 A | 6/2009 |
| CN | 101878002 A | 11/2010 |
| DE | 337437 C | 5/1921 |
| DE | 2830566 A1 | 1/1980 |
| DE | 3339259 C1 | 3/1985 |
| DE | 3447365 A1 | 7/1986 |
| DE | 3717871 A1 | 12/1988 |
| DE | 3925488 A1 | 2/1990 |
| DE | 3902249 A1 | 8/1990 |
| DE | 3920320 A1 | 1/1991 |
| DE | 4016704 C1 | 9/1991 |
| DE | 4219939 A1 | 12/1993 |
| DE | 4421153 A1 | 12/1995 |
| EP | 97001 A1 | 12/1983 |
| EP | 114505 A1 | 8/1984 |

(56) References Cited

FOREIGN PATENT DOCUMENTS

| | | |
|---|---|---|
| EP | 326768 A2 | 8/1989 |
| EP | 337901 A1 | 10/1989 |
| EP | 579868 A2 | 1/1994 |
| EP | 0645984 A1 | 4/1995 |
| EP | 650706 A1 | 5/1995 |
| EP | 677274 A2 | 10/1995 |
| EP | 709061 A1 | 5/1996 |
| EP | 0756735 A1 | 2/1997 |
| EP | 904158 A1 | 3/1999 |
| EP | 908836 A2 | 4/1999 |
| EP | 916324 A2 | 5/1999 |
| EP | 1013231 A2 | 6/2000 |
| EP | 1020734 A2 | 7/2000 |
| EP | 1136041 A2 | 9/2001 |
| EP | 1321097 A2 | 6/2003 |
| EP | 1321107 A1 | 6/2003 |
| EP | 1348393 A1 | 10/2003 |
| EP | 1437102 A1 | 7/2004 |
| EP | 1444957 A1 | 8/2004 |
| EP | 1486900 A1 | 12/2004 |
| EP | 1498851 A1 | 1/2005 |
| EP | 1669033 A1 | 6/2006 |
| EP | 1938749 A2 | 7/2008 |
| EP | 2042126 A1 | 4/2009 |
| FR | 1111677 A | 3/1956 |
| FR | 2429582 A1 | 1/1980 |
| FR | 2659226 A1 | 9/1991 |
| FR | 2679766 A1 | 2/1993 |
| FR | 2721195 A1 | 12/1995 |
| FR | 2768916 A1 | 4/1999 |
| FR | 2819168 A1 | 7/2002 |
| FR | 2838626 A1 | 10/2003 |
| GB | 2094590 A | 9/1982 |
| GB | 2197790 A | 6/1988 |
| GB | 2426200 A | 11/2006 |
| GB | 2437003 A | 10/2007 |
| GB | 2442441 A | 4/2008 |
| JP | 59157715 A | 9/1984 |
| JP | 50231208 A | 11/1985 |
| JP | 2002291706 A | 10/2002 |
| JP | 2008522665 A | 7/2008 |
| JP | 2008523962 A | 7/2008 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | I231755 B | 5/2005 |
| WO | 8807840 A1 | 10/1988 |
| WO | 8909028 A1 | 10/1989 |
| WO | 8911257 A1 | 11/1989 |
| WO | 9107139 A1 | 5/1991 |
| WO | 9325157 A1 | 12/1993 |
| WO | 9413218 A1 | 6/1994 |
| WO | 9414366 A2 | 7/1994 |
| WO | 9528688 A1 | 10/1995 |
| WO | 9607361 A1 | 3/1996 |
| WO | 9729703 A1 | 8/1997 |
| WO | 9730641 A1 | 8/1997 |
| WO | 9730648 A1 | 8/1997 |
| WO | 9732671 A1 | 9/1997 |
| WO | 9800072 A1 | 1/1998 |
| WO | 9832384 A1 | 7/1998 |
| WO | 9901073 A1 | 1/1999 |
| WO | 9932045 A1 | 7/1999 |
| WO | 9952473 A1 | 10/1999 |
| WO | 9959106 A1 | 11/1999 |
| WO | 0170142 A1 | 9/2001 |
| WO | 0184479 A1 | 11/2001 |
| WO | 0218019 A1 | 3/2002 |
| WO | 0222014 A1 | 3/2002 |
| WO | 0226145 A1 | 4/2002 |
| WO | 0236024 A1 | 5/2002 |
| WO | 0237935 A2 | 5/2002 |
| WO | 02067783 A2 | 9/2002 |
| WO | 02096268 A2 | 12/2002 |
| WO | 03042968 A1 | 5/2003 |
| WO | 03051210 A2 | 6/2003 |
| WO | 03051211 A1 | 6/2003 |
| WO | 03077101 A2 | 9/2003 |
| WO | 2004000139 A1 | 12/2003 |
| WO | 2004017842 A2 | 3/2004 |
| WO | 2004032806 A1 | 4/2004 |
| WO | 2004049981 A2 | 6/2004 |
| WO | 2004051301 A2 | 6/2004 |
| WO | 2004061744 A2 | 7/2004 |
| WO | 2004069041 A2 | 8/2004 |
| WO | 2004070580 A2 | 8/2004 |
| WO | 2004075771 A1 | 9/2004 |
| WO | 2004078069 A2 | 9/2004 |
| WO | 2004084725 A1 | 10/2004 |
| WO | 2005018453 A1 | 3/2005 |
| WO | 2005027755 A1 | 3/2005 |
| WO | 2005051239 A1 | 6/2005 |
| WO | 2005051240 A1 | 6/2005 |
| WO | 2005053564 A2 | 6/2005 |
| WO | 2005077039 A2 | 8/2005 |
| WO | 2005084558 A1 | 9/2005 |
| WO | 2005099636 A1 | 10/2005 |
| WO | 2005119505 A2 | 12/2005 |
| WO | 2006058057 A2 | 6/2006 |
| WO | 2006060795 A1 | 6/2006 |
| WO | 2006069260 A1 | 6/2006 |
| WO | 2006092600 A1 | 9/2006 |
| WO | 2006127486 A2 | 11/2006 |
| WO | 2006134345 A1 | 12/2006 |
| WO | 2007036699 A1 | 4/2007 |
| WO | 2007041375 A2 | 4/2007 |
| WO | 2007053572 A2 | 5/2007 |
| WO | 2007062079 A2 | 5/2007 |
| WO | 2007092841 A2 | 8/2007 |
| WO | 2007097853 A2 | 8/2007 |
| WO | 2007097854 A2 | 8/2007 |
| WO | 2007137327 A1 | 12/2007 |
| WO | 2007145937 A2 | 12/2007 |
| WO | 2008014618 A1 | 2/2008 |
| WO | 2008021494 A2 | 2/2008 |
| WO | 2008040961 A1 | 4/2008 |
| WO | 2008044055 A1 | 4/2008 |
| WO | 2008101090 A2 | 8/2008 |
| WO | 2008112996 A1 | 9/2008 |
| WO | 2008117028 A1 | 10/2008 |
| WO | 2008138137 A1 | 11/2008 |
| WO | 2008140748 A1 | 11/2008 |
| WO | 2009001083 A1 | 12/2008 |
| WO | 2009025783 A1 | 2/2009 |
| WO | 2009045960 A1 | 4/2009 |
| WO | 2009076296 A2 | 6/2009 |
| WO | 2009111512 A2 | 9/2009 |
| WO | 2009129063 A1 | 10/2009 |
| WO | 2009129067 A1 | 10/2009 |
| WO | 2010033431 A1 | 3/2010 |
| WO | 2015121400 A1 | 8/2015 |
| WO | 2017004669 A1 | 1/2017 |

OTHER PUBLICATIONS

European Search Report for European Patent Application No. 10150487.6-2310, dated May 12, 2010, 6 pages.
European Search Report for European Patent Application No. 0917188.7-2310, dated Sep. 24, 2010, 7 pages.
Chinese First Office Action, Chinese Patent Application No. 200880118434.4, dated Sep. 7, 2011, 12 pages.
The Vision and Reality of Wearable Computing, XP-002399700, Apr. 1, 2004, 3 pages.
Extended European Search Report, European Application No. 19182307.9, dated Nov. 5, 2019, 7 pages.
PCT International Search Report for International Application No. PCT/US2011/025907, dated Apr. 12, 2011.

(56) References Cited

OTHER PUBLICATIONS

European Search Report; European Patent Application No. 08165418.8-2165; dated Jan. 23, 2009; 6 pages.
Hube et al.; Orthopaedic Surgery The Essentials, Chaper 36 Knee Reconstruction; 1999; 12 pages.
Corin Medical Limited; The Corin X-ActTM Instrumentation and Operative Technique; Nov. 1998; 9 pages.
Kraus et al.; A Comparative Assessment of Alignment Angle of the Knee by Radiographic and Physical Examination Methods; Jun. 6, 2005; 6 pages.
Depuy; LCS Total Knee System—Surgical Procedure; 1989; 36 pages.
Engh et al.; Legent II Surgical Technique; The Concept of Personalization—Total Knee Replacement Using the AMK—Legend II; 1992; 31 pages.
Lotke; Knee Arthroplasty; Primary Total Knees—Standard Principles and Techniques; Raven Press, Ltd.; 5 pages; 1995.
Mills et al.; Use of Computer Tomographic Reconstruction in Planning Osteotomies of the Hip; Jan. 1992; 6 pages.
Radermacher et al.; Image Guided Orthopedic Surgery Using Individual Templates; 10 pages.
Radermacher et al.; Computer Assisted Matching of Planning and Execution in Orthopedic Surgery; 1993; 2 pages.
Radermacher et al.; Technique for Better Execution of CT Scan Planned Orthopedic Surgery on Bone Structures; 9 pages.
Radermacher et al.; Computer Assisted Orthopaedic Surgery with Image Based Individual Templates; No. 354, pp. 28-38; 1998; 11 pages.
Sharma et al.; The Role of Knee Alignment in Disease Progression and Functional Decline in Knee Osteoarthritis; Jul. 11, 2001; American Medical Association; 10 pages.
Berry, Seedhom, et al., "Personalised image-based templates for intra-operative guidance," Proceedings of the Institution of Mechanical Engineers, Part H: Journal of Engineering in Medicine, 111-118, 2005.
SurgiTAIX AG, "OrthoTAIX for Orthopaedic Surgery." Available at http://www.surgitaix.com/Products/OrthoTAIX/OrthoTAIX.pdf.
Radermacher et al., "Computer-Integrated Orthopaedic Surgery: Connection of Planning and Execution in Surgical Intervention," Computer Integrated Surgery, 451-463, 1995.
Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P Nolte and R. Ganz, eds, 42-52, Hogrefe & Huber Publishing 1999.
Portheine et al.; Development of a clinical demonstrator fro computer assisted orthopedic surgery with CT-image based individual templates; 1997; 6 pages.

* cited by examiner

CUSTOMIZED PATIENT-SPECIFIC ORTHOPAEDIC SURGICAL INSTRUMENT

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient-specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to an aspect of the disclosure, an orthopaedic surgical instrument includes a customized patient-specific surgical instrument having a body. A cutting guide slot extends through the body. A pair of first arms extends posteriorly from the body. Each arm includes a first customized patient-specific negative contour configured to receive a portion of a first corresponding positive contour of one of a patient's femoral condyles. A second arm extends proximally from the body. The second arm has a second customized patient-specific negative contour configured to receive a portion of a second corresponding positive contour of an anterior surface of the patient's femur. An alignment slot extends through the body and the proximally extending arm and is positioned to align with a deepest portion of a trochlear groove of the patient's femur when the customized patient-specific surgical instrument is positioned on the patient's femur.

In some embodiments, the alignment slot may extend transverse to the cutting guide slot.

In some embodiments, the body may have a planar distal surface and a planar proximal surface. The alignment slot may include an opening extending through the distal surface and an opening extending through the proximal surface.

In some embodiments, the second arm may include a trunk extending from the body and a flange attached to a proximal end of the trunk. The flange may include a portion of the second customized patient-specific negative contour. The trunk may include an anterior surface and a posterior surface. The alignment slot may include an opening extending through the anterior surface and an opening extending through the posterior surface. The opening extending through the anterior surface and the opening extending through the posterior surface may be curved.

In some embodiments, the customized patient-specific surgical instrument may include a boss attached to, and extending from, the body to a free end spaced apart from the body. The boss may include an opening that is defined in its free end. A guide hole may extend through the boss.

According to another aspect of the disclosure, an orthopaedic surgical instrument includes a customized patient-specific surgical instrument having a body. A cutting guide slot may extend through the body. A pair of first arms may extend posteriorly from the body. Each arm may include a first customized patient-specific negative contour configured to receive a portion of a first corresponding positive contour of one of a patient's femoral condyles. An alignment slot may extend through the body transverse to the cutting guide slot and is positioned to align with a deepest portion of a trochlear groove of the patient's femur when the customized patient-specific surgical instrument is positioned on the patient's femur.

In some embodiments, the body may have a planar distal surface and a planar proximal surface. The alignment slot may include an opening extending through the distal surface and an opening extending through the proximal surface.

In some embodiments, the customized patient-specific surgical instrument may include a boss attached to, and extending from, the body to a free end spaced apart from the body. The boss may include an opening that is defined in its free end. A guide hole may extend through the boss.

In some embodiments, a second arm may extend proximally from the body. The second arm may include a trunk extending from the body and a flange attached to a proximal end of the trunk. The second arm may have a second customized patient-specific negative contour configured to receive a portion of a second corresponding positive contour of an anterior surface of the patient's femur. The flange may include a portion of the second customized patient-specific negative contour. The trunk may include an anterior surface and a posterior surface. The alignment slot may include an opening extending through the anterior surface and an opening extending through the posterior surface. The opening extending through the anterior surface and the opening extending through the posterior surface may be curved.

According to yet another aspect of the disclosure, a method of performing an orthopaedic surgical procedure includes placing a visual marking on a surface defining a deepest portion of a trochlear groove of a patient's femur. The method also includes placing a customized patient-specific surgical instrument on the patient's femur. The method also includes aligning an alignment slot extending through the customized patient-specific surgical instrument with the visual marking on the surface of the patient's femur to position the customized patient-specific surgical instrument on the patient's femur.

In some embodiments, the method may include aligning an alignment slot extending through a body of the customized patient-specific surgical instrument with the visual marking.

In some embodiments, the method may include aligning an alignment slot extending through an arm of the customized patient-specific surgical instrument with the visual marking.

BRIEF DESCRIPTION OF THE DRAWINGS

The detailed description particularly refers to the following figures, in which.

DETAILED DESCRIPTION OF THE DRAWINGS

Figure 1:
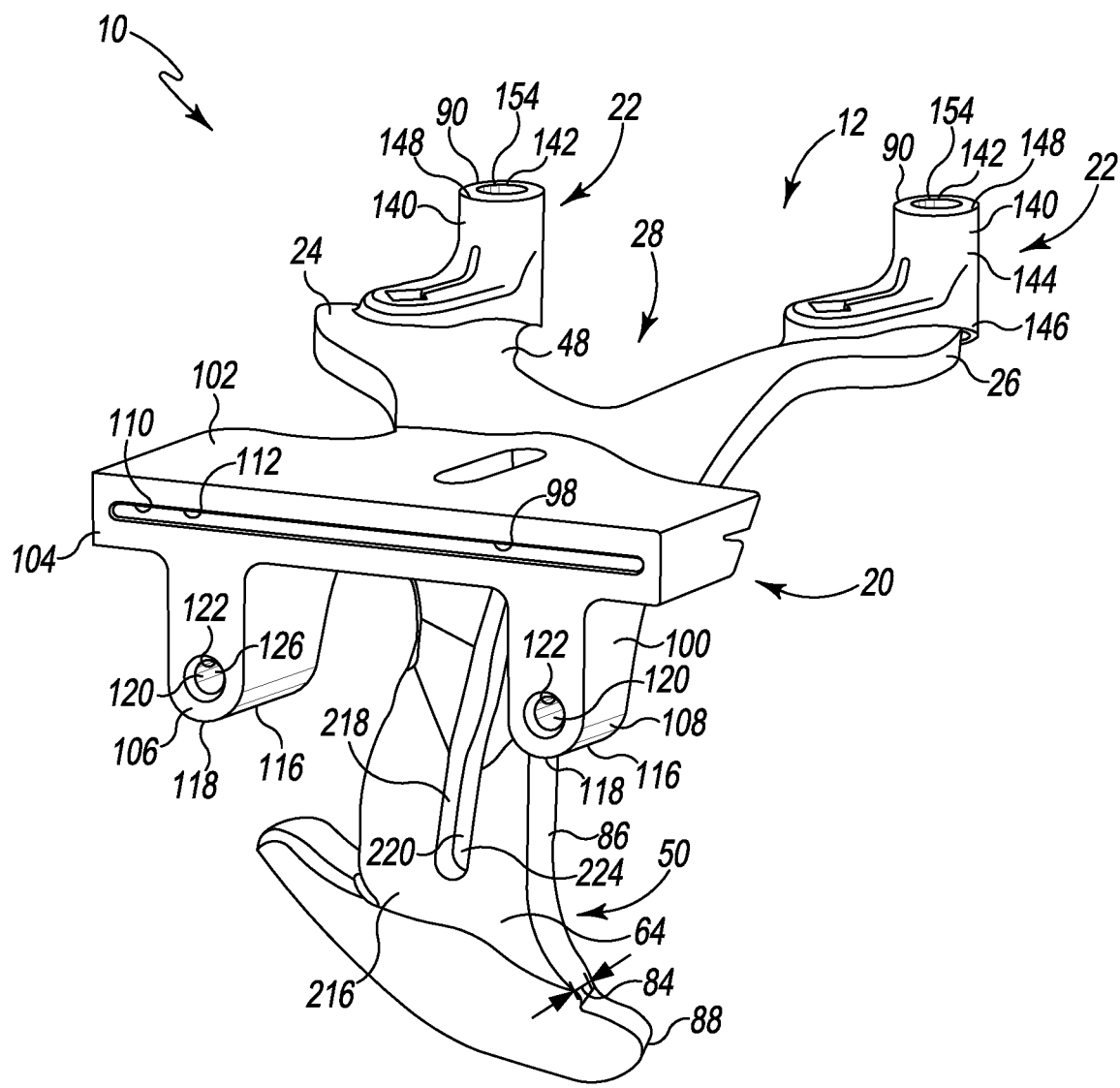
FIG. 1 is a perspective view of a customized patient-specific surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument 10 is shown. The instrument 10 is illustratively a customized patient-specific orthopaedic surgical instrument. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient-specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides.

The customized patient-specific orthopaedic surgical instrument is a femoral cutting guide block 12 in the illustrative embodiment. The anterior contact surfaces and the distal contact surfaces of the cutting block 12 facilitate securing the cutting block 12 on the patient's femur. As described in greater detail below, the surgical instrument 10 is configured to be coupled to the patient's femur in a unique pre-determined location and orientation on the patient's condyles and an anterior portion of the femur extending proximally from the condyles. The cutting block 12 contact regions are configured to couple to the patient's femur in a unique pre-determined location and orientation so that an alignment slot extending through the cutting block 12 is aligned with the deepest portion of the trochlear groove. In the illustrative embodiment, the structure of the cutting block 12 has been contoured to reduce its size relative to conventional cutting blocks and avoid contact with undesirable regions of the patient's bone.

The femoral cutting block 12 includes a base plate 20 and a number of surgical tool guide bodies 22 that are attached to, and extend outwardly from, the base plate 20. In the illustrative embodiment, the femoral cutting block 12 is a single monolithic component formed from a metallic material such as, for example, stainless steel. In that way, the base plate 20 and the guide bodies 22 form a single monolithic metallic block. The femoral cutting block 12 is formed by, for example, Direct Metal Laser Sintering (DMLS), also known as Selective Laser Sintering (SLS), which is a form of additive manufacturing technology. In DMLS, the femoral cutting block 12 is formed in a layer-by-layer fashion using laser sintering in which light fuses metallic powder, forming the metallic structures that define the femoral cutting block 12. It should be appreciated that other forms of additive manufacturing technology such as, for example, optical fabrication, photo-solidification, or resin printing may be used to fabricate the femoral cutting block 12.

Figure 7:
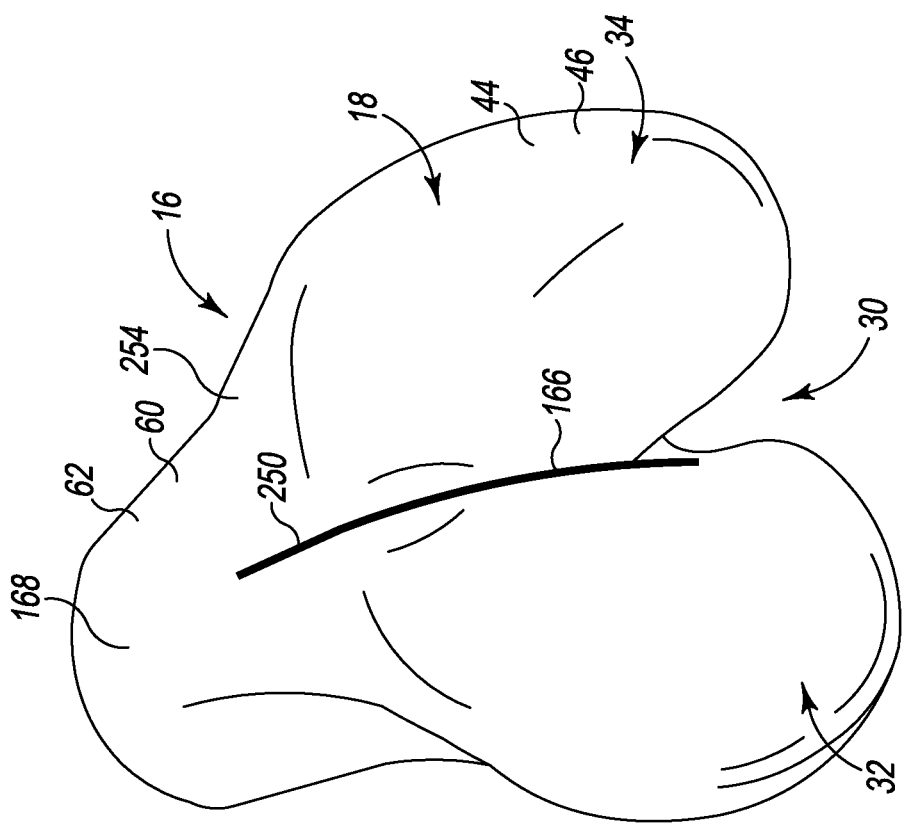
FIG. 7 is a perspective view of distal end of a patient's femur.

The base plate 20 includes a pair of arms 24, 26 that are configured to engage the distal end 18 of the patient's femur 16 (see FIG. 7). The arms 24, 26 are spaced apart from each other such that a notch 28 is defined between the inner edges of the arms 24, 26. The notch 28 is sized and shaped to correspond to the natural intercondylar notch 30 of the patient's femur 16, which is defined between the natural condyles 32, 34 of the patient's femur 16 (see FIG. 7).

Figure 2:
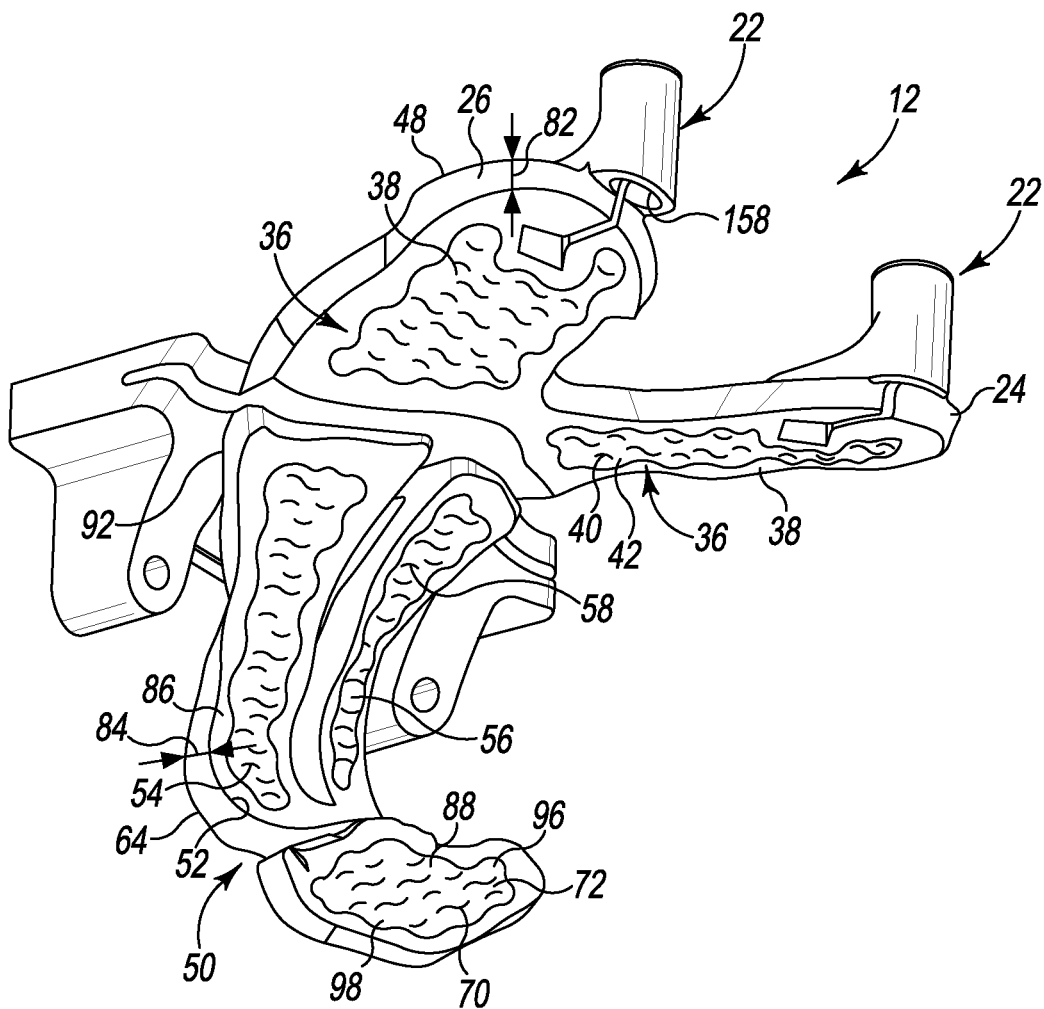
FIG. 2 is a bottom perspective view of the customized patient-specific surgical instrument shown in FIG. 1.

Each of the arms 24, 26 has a bone-contacting or bone-facing surface 36 (shown in FIG. 2) that engages one of the natural condyles 32, 34. In the illustrative embodiment, each bone-facing surface 36 includes a number of negative contours 38 that are configured to receive a portion of the natural condyles 32, 34. Each contour 38 has a unique set of ridges 40 and depressions 42 that are shaped to engage a corresponding unique set of depressions 44 and ridges 46 of the natural femoral condyles 32, 34 (see FIG. 7). Each of the arms 24, 26 also includes an outer surface 48 that is positioned opposite its corresponding bone-facing surface 36. In the illustrative embodiment, each outer surface 48 is substantially smooth. As used herein, the term "substantially" should be understood to refer to the normal tolerances created by manufacturing variation and other design criteria. As such, a "substantially smooth surface" is one that is smooth within the normal tolerances created or permitted by manufacturing variation and other design criteria.

The base plate 20 also includes a proximally extending arm 50 that is configured to engage the distal end 18 of the patient's femur 16. The proximally extending arm 50 includes a trunk 86 and a flange 88 extending proximally from the trunk 86. The trunk 86 includes a base 92 having first width 94 between a pair of edges 66, 68. The trunk 86 extends proximally and narrows to a point 78 that has a width 130 that is less than the width 94. From the point 78, the trunk 86 flares outward to an end 132 having a width 134 that is greater than the width 130 and less than the width 94. From the point 78 to the end 132, the trunk 86 curves laterally to mimic the curve of the trochlear groove 166. The trunk 86 is generally concave such that the point 78 extends anteriorly of the base 92 and the end 132. The trunk 86 also includes convex and concave portions to receive corresponding concave and convex portions of the patient's femur 16.

The trunk 86 of the proximally extending arm 50 includes a bone-facing surface 52 (shown in FIG. 2) that includes a number of negative contours 54 that are configured to receive a portion of the patient's femur 16. The bone-facing surface 52 extends across the trunk 86 from the base 92 to the end 132. The contour 54 of the trunk 86 has a unique set of ridges 56 and depressions 58 that are shaped to engage a corresponding unique set of depressions 60 and ridges 62 of the patient's femur 16. The proximally extending arm 50 also includes an outer surface 64 that is positioned opposite the bone-facing surface 52. In the illustrative embodiment, the outer surface 64 is substantially smooth.

The trunk 86 is configured to curve with the trochlear groove 166 of the patient's femur 16. As illustrated in FIG. 7, the trochlear groove 166 extends between the natural femoral condyles 32, 34 and ends at an anterior surface 168 of the femur 16, which begins at an end of the natural femoral condyles 32, 34. That is, the natural femoral condyles 32, 34 curve into the anterior surface 168. The trochlear groove 166 also curves laterally between the natural femoral condyles 32, 34. The trunk 86 is configured to follow the path of the trochlear groove 166 so that the flange 88 engages the anterior surface 168 of the patient's femur 16.

The flange 88 extends proximally from the trunk 86 and includes a pair of arms 136 that extend medially and laterally from the trunk 86. The posterior edges 66, 68 extend along the trunk 86 and flange 88. As a result, each of the edges 66, 68 includes convex and concave portions to receive corresponding concave and convex portions of the patient's femur 16. The edges 66, 68 extend around the arms 136 of the flange and meet at a posterior tip 69 that is sized and shaped to be positioned on the anterior surface 168 of the patient's femur 16. The flange 88 includes a bone-facing surface 96 that includes a number of negative contours 98 that are configured to receive a portion of the anterior surface 168 of the patient's femur 16. The contour 98 of the flange 88 has a unique set of ridges 70 and depressions 72 that are shaped to engage a corresponding unique set of depressions 74 and ridges 76 of the anterior surface 168 of the patient's femur 16. The negative contours 38, 54, 98 of the base plate 20 permit the cutting block 12 (and hence the tool guide bodies) to be positioned on the patient's femur 16 in a unique pre-determined location and orientation.

In the illustrative embodiment, the base plate 20 of the cutting block 12 has a low-profile to reduce the size of the incision and reduce the amount of bone displacement needed to position the cutting block 12. The low-profile has been customized for block 12 by minimizing the thicknesses of the arms 24, 26 and the proximally extending arm 50. A thickness 82 is defined between the outer surface 48 and the bone-facing surface 36 of each arm. To minimize the thickness 82, the outer surface 48 of each arm is convexly curved to follow the concave curvature of the bone-facing surface 36. Similarly, a thickness 84 is defined between the outer surface 64 and the bone-facing surface 52 of the proximally extending arm 50, and the outer surface 64 of the arm 50 is shaped to follow the geometry of the bone-facing surface 52 to minimize the thickness 84.

Each of the surgical tool guide bodies 22 of the cutting block 12 is attached to and extends outwardly from the outer surfaces 48, 64 of the arms 24, 26 and the proximally extending arm 50 to a free end 90 that is spaced apart from the base plate 20. In the illustrative embodiment, the guide bodies 22 include an anterior guide body 100 that extends anteriorly from the anterior ends of the arms 24, 26 and the proximally extending arm 50 to its free end 102. The anterior guide body 100 includes a distal flange 104 and a pair of bosses 106, 108 that extend proximally from the flange 104.

Figure 3:
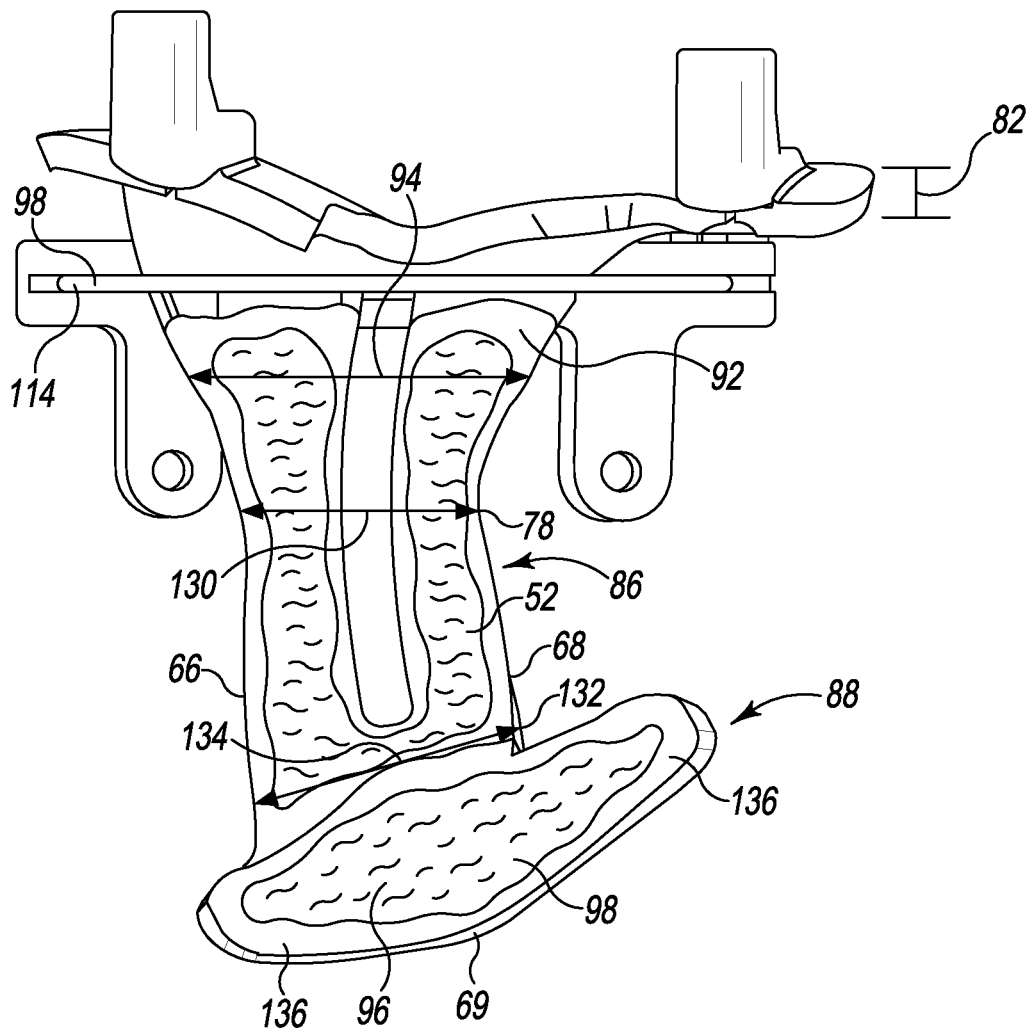
FIG. 3 is a rear elevation view of the customized patient-specific surgical instrument shown in FIG. 1.

The distal flange 104 of the anterior guide body 100 includes an elongated opening 110 that is defined in the free end 102 and a number of inner walls 112 that extend inwardly from the opening 110. As shown in FIG. 3, the inner walls 112 extend to another opening 114 that is defined in the bone-facing surface 52. The opening 114 extends through the contour 54 of the base plate 20 such that the opening 114 is defined by the edges 66, 68 of the bone-facing surface 52, which follow a curved, irregular path that matches the shape of the patient's femur 16 in that region. The opening 114 cooperates with the inner walls 112 and the elongated opening 110 to define the guide slot 98, which is sized and shaped to guide a surgical tool such as, for example, a cutting blade, into engagement with the patient's bone. As described above, the cutting guide slot 98 is positioned to guide a customized, patient-specific resection of the distal end 18 of the patient's femur 16. Because the edge 66 follows the shape of the patient's femur 16 and the posterior tip of the edge 66 extends into the patient's trochlear groove, the cutting guide slot 98 provides support for the cutting blade in close proximity to the region under resection.

Figure 4:
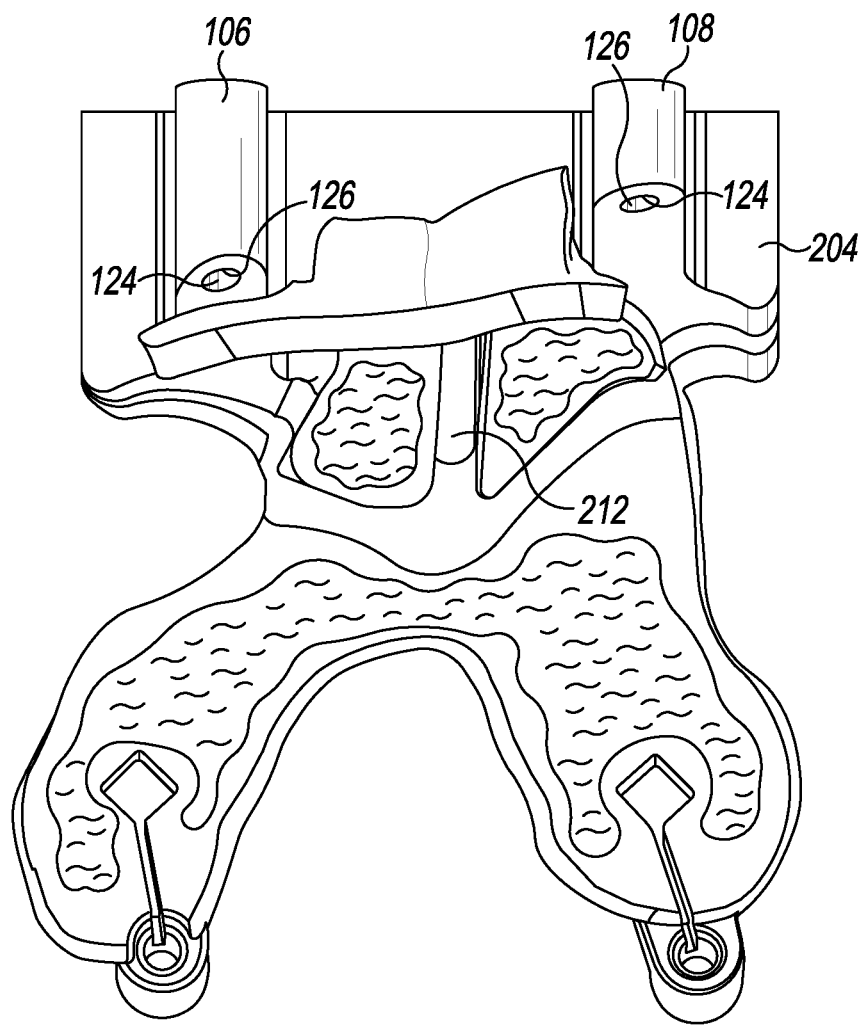
FIG. 4 is another bottom perspective view of the customized patient-specific surgical instrument shown in FIG. 1.

As shown in FIG. 1, each of the bosses 106, 108 extend from a proximal surface 116 of the distal flange 104 to a curved proximal end 118. It should be appreciated that in other embodiments one or both of the bosses 106, 108 may be spaced apart from the distal flange 104, thereby forming separate guide bodies. An opening 120 is defined in the free end 102 of each of the bosses 106, 108 adjacent to the proximal end 118. An inner wall 122 extends inwardly from the opening 120. As shown in FIG. 4, each inner wall 122 extends to another opening 124 to define a guide slot 126 extending through the cutting block 12. In the illustrative embodiment, each guide slot 126 is a drill guide and fixation pin guide hole, which is sized and shaped to guide a surgical drill to prepare the patient's bone to receive a fixation pin to couple the block 12 to the bone.

The guide bodies 22 include a pair of posterior guide bosses 140, which are attached to, and extend distally from, the outer surfaces 48 of the arms 24, 26, respectively. Each posterior guide boss 140 includes a guide slot 142 that is sized and shaped to guide a surgical drill and a fixation pin into engagement with the patient's bone to couple the block 12 to the bone. Each guide boss 140 includes a post 144 that extends from a base 146 attached to the outer surface 48 of one of the arms 24, 26 to a free end 148 that is spaced apart from the outer surface 48.

An opening 154 is defined in the free end 148 of each boss 140. An inner wall 178 extends inwardly from the opening 154 to another opening 158 (shown in FIG. 2) that is defined in a bone-facing surface 36 of one of the arms 24, 26. The openings 154, 158 and the inner wall 178 cooperate to define the guide slot 142. As described above, each guide slot 142 is a drill guide and fixation pin guide hole, which is sized and shaped to guide a surgical drill or self-drilling fixation pin to prepare the patient's bone to receive a fixation pin to couple to the block 12 to the bone.

Figure 6:
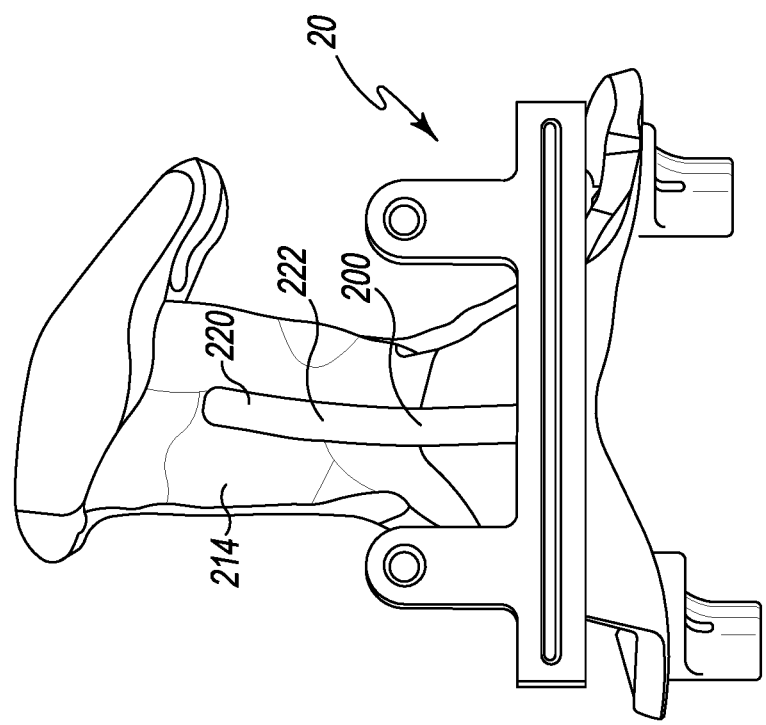
FIG. 6 is a front elevation view of the customized patient-specific surgical instrument shown in FIG. 1.
Figure 5:
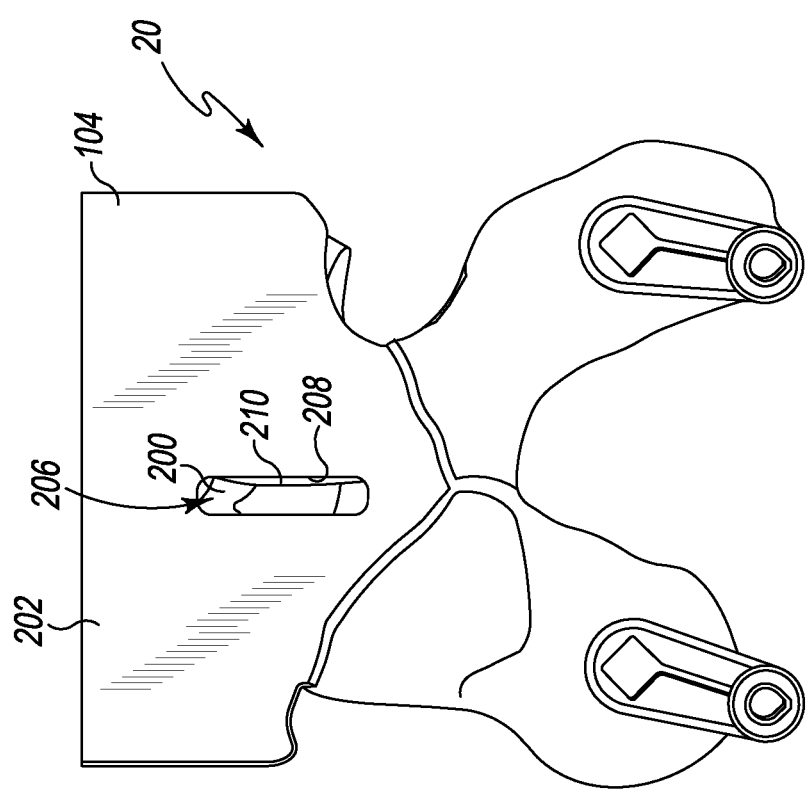
FIG. 5 is a top plan view of the customized patient-specific surgical instrument shown in FIG. 1.

Referring to FIGS. 5-6, the base plate 20 includes an alignment slot 200 positioned to align with a deepest portion of the patient's natural trochlear groove 166. The distal flange 104 has a planar distal surface 202 and a planar proximal surface 204 (shown in FIG. 4). A distal end 210 of the alignment slot 200 is defined by inner walls 208 extending between an opening 206 in the distal surface 202 and an opening in the inner walls 112 of the elongated opening 110. The distal end 212 of the alignment slot 200 is also defined by inner walls 230 extending between an opening in the inner walls 112 of the elongated opening 110 and an opening 212 in the proximal surface 204. The distal end 210 of the alignment slot 200 extends transverse to the cutting guide slot 98.

The bone-facing surface 52 of the trunk 86 of the proximally extending arm 50 forms a posterior surface 214 of the trunk 86, and the outer surface 64 forms an anterior surface 216 (shown in FIG. 1) of the trunk 86. A proximal end 220 of the alignment slot 200 is defined by inner walls 218 extending between an opening 222 in the posterior surface 214 and an opening 224 in the anterior surface 216. The proximal end 220 of the alignment slot 200 extends transverse to the cutting guide slot 98. In the illustrative embodiment, the proximal end 220 of the alignment slot 200 is curved both laterally and in a concave shape to match a contour of the trunk 86 and the deepest portion of the patient's natural trochlear groove 166. The distal end 210 and the proximal end 220 of the alignment slot 200 extend from one another to form a continuous alignment slot 200 that is transverse to the cutting guide slot 98.

Prior to surgery, a three-dimensional model of the patient's femur 16 is developed based on scans of the patient's femur 16. The scans may include a magnetic resonance image, a computed tomography image, a plurality of x-ray images, or the like. The cutting block 12 is manufactured to include negative contours that match the positive contours of the three-dimensional model. Additionally the alignment slot 200 is formed in the cutting block 12 to match the position of the deepest portion of the patient's natural trochlear groove 166. Creating the cutting block 12 based on the three-dimensional model facilitates ensuring a correct alignment of the cutting block 12 on the patient's femur 16.

Referring now to FIG. 7, during use, a surgeon prepares the patient's femur 16 by placing a visual indicator 250 on the deepest portion of the patient's natural trochlear groove 166. In the illustrative embodiment, the visual indicator 250 is a line drawn on the deepest portion of the patient's natural trochlear groove 166. The cutting block 12 is then positioned on a distal end 18 of the patient's femur 16 so that the unique set of ridges 40 and depressions 42 engage the corresponding unique set of depressions 44 and ridges 46 of the natural condyles 32, 34 and the unique set of ridges 56 and depressions 58 engage the corresponding unique set of depressions 60 and ridges 62 of an anterior side 254 of the patient's femur 16. The unique set of ridges 70 and depressions 72 of the flange 88 are also positioned to engage the corresponding unique set of depressions 74 and ridges 76 of the anterior surface 168 of the patient's femur 16.

Figure 8:
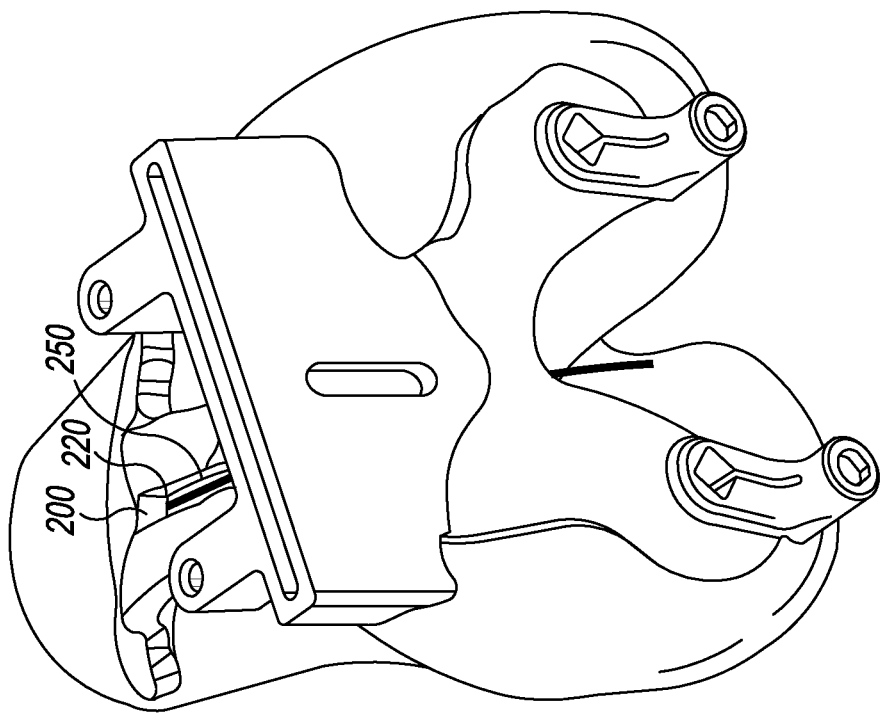
FIG. 8 is a perspective view of the customized patient-specific surgical instrument of FIG. 1 positioned on the distal end of the patient's femur of FIG. 7.
Figure 9:
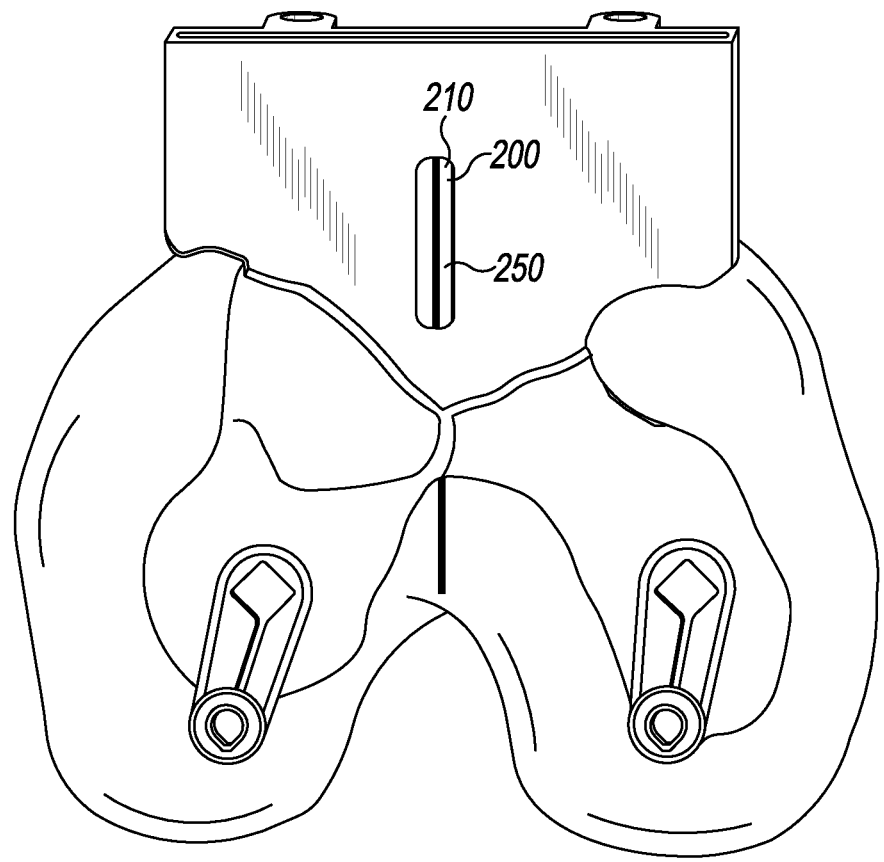
FIG. 9 is an elevation view of the customized patient-specific surgical instrument of FIG. 1 positioned on the distal end of the patient's femur of FIG. 7.

The surgeon verifies the alignment of the cutting block 12 on the femur 16 by aligning the visual indicator 250 with the alignment slot 200. As illustrated in FIG. 8, the proximal end 220 of the alignment slot 200 is aligned with a portion of the visual indicator 250 that extends along the anterior side 254 of the patient's femur. As illustrated in FIG. 9, the distal end 210 of the alignment slot 200 is aligned with a portion of the visual indicator 250 that extends along the distal end 18 of the patient's femur 16 and extends between the natural condyles 32, 34.

The surgeon can then position a fixation pin in each of the guide slots 126 and 142 to secure the cutting block 12 to the patient's femur. A distal resection is then performed on the distal end 18 of the patient's femur 16 by advancing a surgical saw through the guide slot 98. In some embodiments, the fixation pins inserted through the guide slots 142 may be removed before the distal resection of the distal end 18 of the patient's femur 16 so that the fixation pins do not interfere with the surgical saw.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic surgical instrument, comprising:
   a customized patient-specific surgical instrument comprising:
   a body having a planar distal surface and a planar proximal surface,
   a cutting guide slot extending through the body,
   a pair of first arms extending posteriorly from the body, each arm including a first customized patient-specific negative contour configured to receive a portion of a first corresponding positive contour of one of a patient's femoral condyles,
   a second arm extending proximally from the body, the second arm having a second customized patient-specific negative contour configured to receive a portion of a second corresponding positive contour of an anterior surface of the patient's femur, and an alignment slot extending through the body and the proximally extending arm and positioned to align with a deepest portion of a trochlear groove of the patient's femur when the customized patient-specific surgical instrument is positioned on the patient's femur wherein (i) the alignment slot includes a slot portion extending through the body transverse to the cutting guide slot, and (ii) the slot portion includes a first opening extending traverse to the cutting guide slot through the planar distal surface and a second opening aligned with the first opening and extending traverse to the cutting guide slot through the planar proximal surface.

2. The orthopaedic surgical instrument of claim 1, wherein the second arm includes a trunk extending from the body and a flange attached to a proximal end of the trunk, wherein the flange includes a portion of the second customized patient-specific negative contour.

3. The orthopaedic surgical instrument of claim 2, wherein the trunk includes an anterior surface and a posterior surface, wherein the alignment slot includes an opening extending through the anterior surface and an opening extending through the posterior surface.

4. The orthopaedic surgical instrument of claim 3, wherein the opening extending through the anterior surface and the opening extending through the posterior surface are curved.

5. The orthopaedic surgical instrument of claim 1, wherein the customized patient-specific surgical instrument includes a boss attached to, and extending from, the body to a free end spaced apart from the body, the boss including an opening that is defined in its free end.

6. The orthopaedic surgical instrument of claim 5, including a guide hole extending through the boss.

\* \* \* \* \*